(12) United States Patent
Zheng et al.

(10) Patent No.: US 9,826,861 B2
(45) Date of Patent: Nov. 28, 2017

(54) WATER OUTPUT DEVICE HAVING ULTRASONIC PULVERIZING FUNCTION AND METHOD OF IMPLEMENTING THE SAME

(71) Applicant: Xiamen Runner Industrial Corporation, Xiamen (CN)

(72) Inventors: Shun-chuan Zheng, Xiamen (CN); Chun-hui Lin, Xiamen (CN); He-sheng Chen, Xiamen (CN); Cheng Lin, Xiamen (CN); Wen Gao, Xiamen (CN)

(73) Assignee: XIAMEN RUNNER INDUSTRIAL CORPORATION, Xiamen (CN)

( * ) Notice: Subject to any disclaimer, the term of this patent is extended or adjusted under 35 U.S.C. 154(b) by 0 days.

(21) Appl. No.: 15/188,990

(22) Filed: Jun. 22, 2016

(65) Prior Publication Data
US 2017/0066002 A1 Mar. 9, 2017

(30) Foreign Application Priority Data

Jul. 3, 2015 (CN) .......................... 2015 1 0384030

(51) Int. Cl.
*A47K 3/28* (2006.01)
*B05B 1/18* (2006.01)
*B05B 17/06* (2006.01)
*A61N 7/00* (2006.01)
*B05B 17/00* (2006.01)

(52) U.S. Cl.
CPC ................ *A47K 3/281* (2013.01); *A61N 7/00* (2013.01); *B05B 1/18* (2013.01); *B05B 17/0646* (2013.01)

(58) Field of Classification Search
CPC ......... B05B 17/00; B05B 17/04; B05B 17/06; B05B 17/0607; B05B 17/0638; B05B 17/0646; B05B 17/0653; B05B 17/0661; B05B 17/0676; B05B 1/18; A47K 3/281; A61N 7/00
USPC ............................................. 239/102.2, 548
See application file for complete search history.

(56) References Cited

U.S. PATENT DOCUMENTS

2015/0069145 A1* 3/2015 Yen ..................... B05B 17/0646
239/102.2

* cited by examiner

*Primary Examiner* — Christopher Kim
(74) *Attorney, Agent, or Firm* — Chun-Ming Shih

(57) ABSTRACT

A water output device having ultrasonic pulverizing function comprises a shower main body, which includes a decoration box, detachably embedded in the shower main body, or forming with the shower main body into a body; and an ultrasonic pulverizing device, disposed in the decoration box. The ultrasonic pulverizing device includes: a water box, with its upper portion provided with a water input port, and with its lower portion provided with a water output port; an ultrasonic wave generator, fixed to a water output port at a lower portion of the water box through a fixing block, and having a web-shape structure inside, for allowing small particles of water mist to pass through; and a control device, disposed at a side of the water box, and including a power source module, a charging module, a vibration circuit module.

9 Claims, 4 Drawing Sheets

WATER OUTPUT DEVICE HAVING ULTRASONIC PULVERIZING FUNCTION AND METHOD OF IMPLEMENTING THE SAME

BACKGROUND OF THE INVENTION

Field of the Invention

The present invention relates to a water output device, and in particular to a water output device having ultrasonic pulverizing function and method of implementing the same.

The Prior Arts

Presently on the market, the shower equipment is designed only to have a single and simple function of providing centrifugal water output for use in shower. As such, the output water particles thus produced are rather large, thus it is not capable of meeting the user demand of moisturizing application, such as facial moisturizing.

Therefore, presently, the design and performance of the water output device is not quite satisfactory, and it leaves much room for improvement.

SUMMARY OF THE INVENTION

In view of the problems and drawbacks of the prior art, the present invention provides a water output device having ultrasonic pulverizing function and method of implementing the same, to overcome the shortcomings of the prior art.

The major objective of the present invention is to provide water output device having ultrasonic pulverizing function, comprising: a shower main body, which includes a decoration box, detachably embedded in the shower main body, or forming with the shower main body into a body; and an ultrasonic pulverizing device, disposed in the decoration box.

In an aspect of the present invention, the ultrasonic pulverizing device includes a water box, an ultrasonic wave generator, and a control device. The water box is configured, with its upper portion provided with a water input port, and with its lower portion provided with a water output port. The ultrasonic wave generator is fixed to a water output port located at a lower portion of the water box through using a fixing block, and it is provided with a web-shape structure inside, for allowing only small particles of water mist to pass through. The control device is disposed at a side of the water box, and it includes a power source module, a charging module, and a vibration circuit module. The charging module and the vibration circuit module are connected respectively to the power source module electrically; the ultrasonic wave generator is connected electrically to the vibration circuit module; while the power source module is fixed in the decoration box through using a battery fixing bar.

In another aspect of the present invention, on the vibration circuit module is provided with a press button and an LED lamp; the decoration box includes a decoration upper cover and a decoration lower cover fastening to each other; on the decoration upper cover is provided with a plastic push button, and a lamp hood slot acting in cooperation with the LED lamp; and a lower portion of the plastic push button acts in cooperation with the push button through a push button hard block.

In yet another aspect of the present invention, on a side of the decoration box is provided with an input port in communication with the water input port, on the input port is provided with input port tight seal plastic, on the side of the decoration box is further provided with an USB insertion port connected electrically to the charging module, and on the USB insertion port is provided with USB tight seal plastic.

In a further aspect of the present invention, a lower portion of the decoration lower cover is protruded downward to form a protrusion, on the protrusion is provided with an output port in communication with a water output port at a lower portion of the water box.

In an aspect of the present invention, in a lower portion of the shower main body is provided with a water output chamber in communication with a water input pipeline of the shower main body; while in a central portion of the water output chamber is provided with a hole to receive the protrusion.

In another aspect of the present invention, the water output chamber includes a water output chamber upper cover and a water output chamber lower cover fastened to each other, the water output chamber upper cover is provided with a water input port in communication with the water input pipeline; a tight seal ring is provided at the connection of the water input port and the water input pipeline; the water output chamber upper cover is fixed to the shower main body through threading; and a plurality of water output ports are provided on the water output chamber lower cover.

In yet another aspect of the present invention, above the water output chamber upper cover is provided with a fixing claw used for fixing the decoration box.

In a further aspect of the present invention, an input port for the water input pipeline of the shower main body is provided with a threaded connector.

The present invention also provides a method of implementing a water output device having ultrasonic pulverizing function, comprising the following steps: press down the plastic push button, to activate the ultrasonic wave generator to work, such that water and essence in the water box is agitated and vibrated by the ultrasonic waves generated, to pass through the web-shape structure in the ultrasonic wave generator allowing only small particles of mist to pass through, to form small particles of water or essence, hereby providing therapy to a user. When power is used up in the decoration box, perform charging to a charging module through a USB insertion port. And when water is used up, add water to a water box.

Compared with the existing technology, the present invention has the following advantages: it is simple in construction, and convenient to use, capable of providing both the showering and pulverizing functions, in achieving facial moisturizing and essence spraying at the same time, while saving the equipment and space that would otherwise be required for this purpose. Further, the decoration box can be taken out alone to achieve pulverizing and moisturizing by itself, in realizing multiple functions of a shower.

Further scope of the applicability of the present invention will become apparent from the detailed descriptions given hereinafter. However, it should be understood that the detailed descriptions and specific examples, while indicating preferred embodiments of the present invention, are given by way of illustration only, since various changes and modifications within the spirit and scope of the present invention will become apparent to those skilled in the art from the detailed descriptions.

BRIEF DESCRIPTION OF THE DRAWINGS

The related drawings in connection with the detailed descriptions of the present invention to be made later are described briefly as follows, in which.

DETAILED DESCRIPTION OF THE PREFERRED EMBODIMENT

The purpose, construction, features, functions and advantages of the present invention can be appreciated and understood more thoroughly through the following detailed descriptions with reference to the attached drawings.

Figure 1:
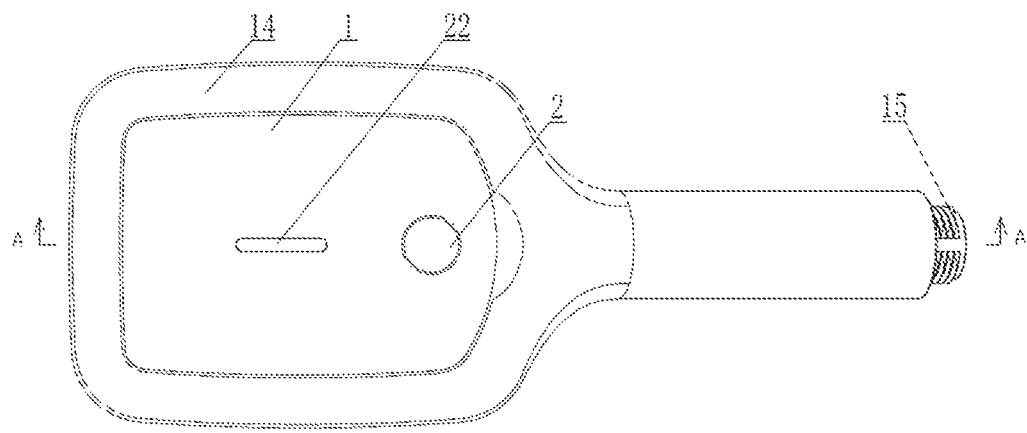
FIG. 1 is a front view of a water output device having ultrasonic pulverizing function according to an embodiment of the present invention.
Figure 2:
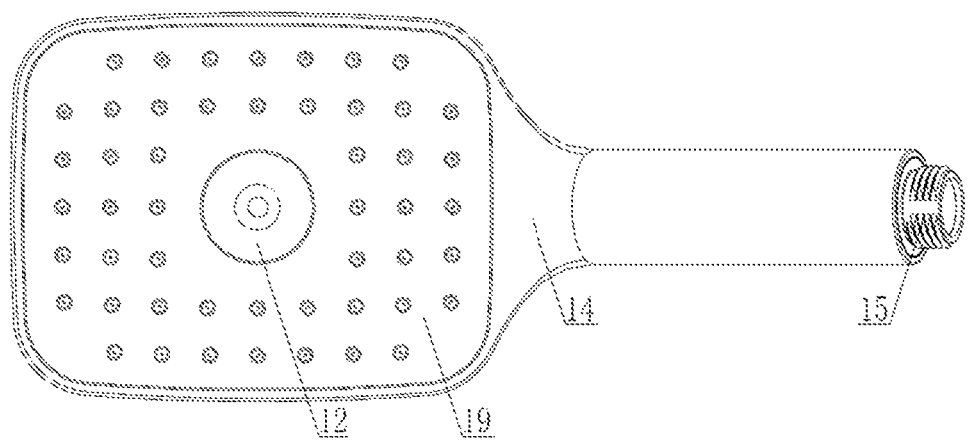
FIG. 2 is a rear view of a water output device having ultrasonic pulverizing function according to an embodiment of the present invention.
Figure 3:
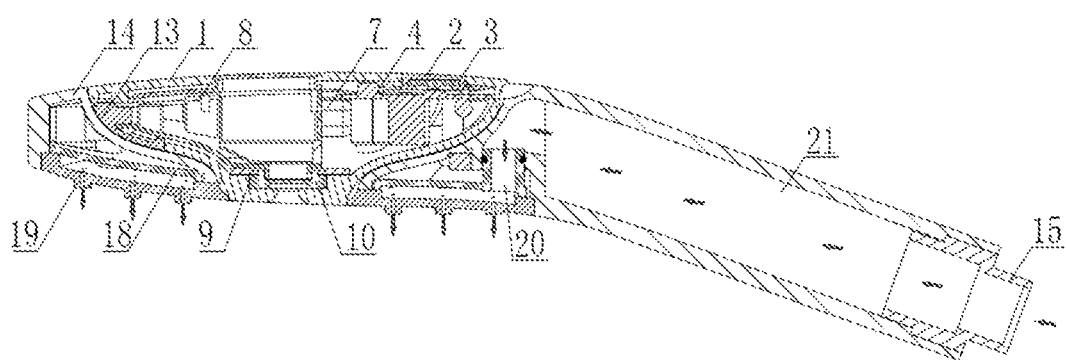
FIG. 3 is a cross section view of water output device having ultrasonic pulverizing function along A-A line of FIG. 1.
Figure 4:
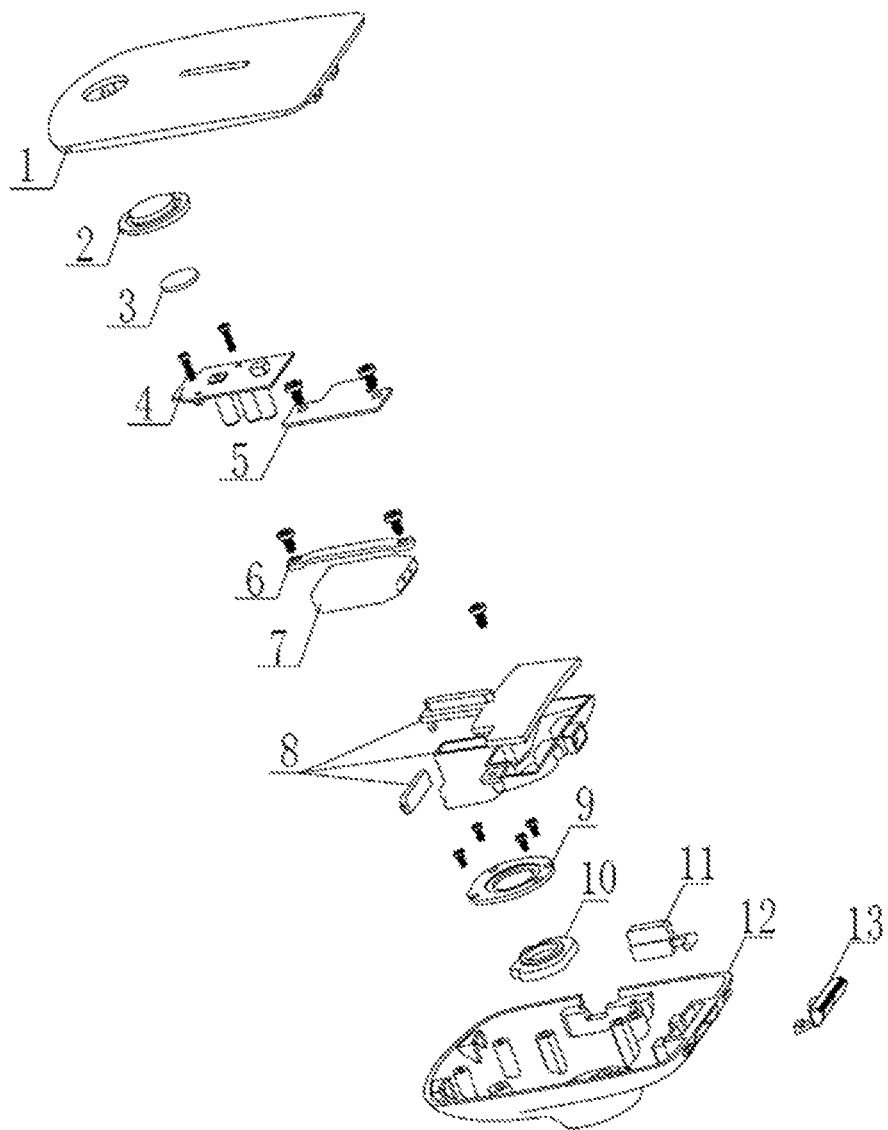
FIG. 4 is an exploded view of a decoration box according to an embodiment of the present invention.
Figure 5:
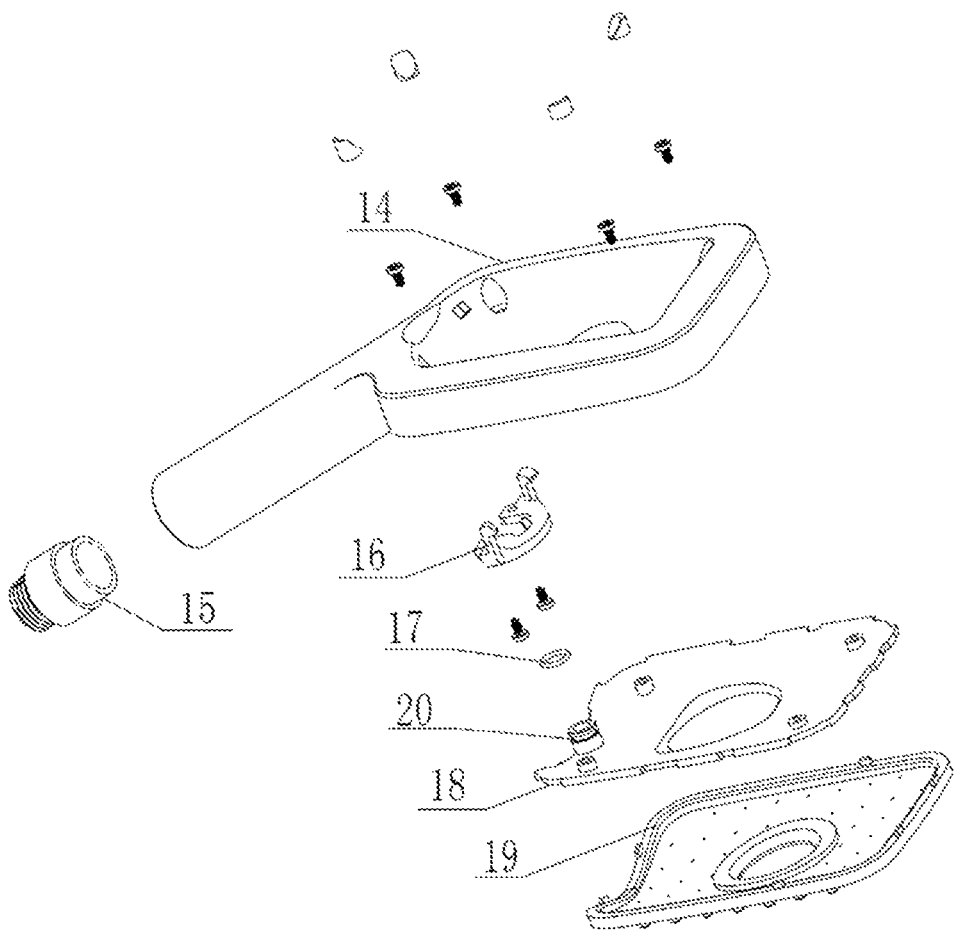
FIG. 5 is an exploded view of a shower main body according to an embodiment of the present invention when the decoration box is removed.

Refer to FIGS. 1 to 5 respectively for a front view of a water output device having ultrasonic pulverizing function according to an embodiment of the present invention; a rear view of a water output device having ultrasonic pulverizing function according to an embodiment of the present invention; a cross section view of water output device having ultrasonic pulverizing function along A-A line of FIG. 1; an exploded view of a decoration box according to an embodiment of the present invention; and an exploded view of a shower main body according to an embodiment of the present invention when the decoration box is removed.

As shown in FIGS. 1 to 5, the present invention provides a water output device having ultrasonic pulverizing function, comprising: a shower main body 14 which includes: a decoration box, detachably embedded in the shower main body 14, or forming with the shower main body 14 into a body; and an ultrasonic pulverizing device, disposed in the decoration box.

In the present embodiment, the ultrasonic pulverizing device includes a water box 8, an ultrasonic wave generator 10, and a control device. The water box 8 is configured, with its upper portion provided with a water input port, and with its lower portion provided with a water output port. The ultrasonic wave generator 10 is fixed to a water output port located at a lower portion of the water box 8 through using a fixing block 9, and it is provided with a web-shape structure inside, for allowing small particles of water mist to pass through. The control device is disposed at a side of the water box 8, and it includes a power source module 7, a charging module 5, and a vibration circuit module 4. The charging module 5 and the vibration circuit module 4 are connected respectively to the power source module 7 electrically; the ultrasonic wave generator 10 is connected electrically to the vibration circuit module 4; while the power source module 7 is fixed in the decoration box through using a battery fixing bar 6.

In the present embodiment, on the vibration circuit module 4 is provided with a press button and an LED lamp; the decoration box includes a decoration upper cover 1 and a decoration lower cover 12 fastening to each other; on the decoration upper cover 1 is provided with a plastic push button 2, and a lamp hood slot 22 acting in cooperation with the LED lamp; and a lower portion of the plastic push button 2 acts in cooperation with the push button through a push button hard block 3.

In the present embodiment, on a side of the decoration box is provided with an input port in communication with the water input port, on the input port is provided with input port tight seal plastic, on the side of the decoration box is further provided with an USB insertion port connected electrically to the charging module 5, and on the USB insertion port is provided with USB tight seal plastic 11.

In the present embodiment, a lower portion of the decoration lower cover 12 is protruded downward to form a protrusion, on the protrusion is provided with an output port in communication with a water output port at a lower portion of the water box 8.

In the present embodiment, in a lower portion of the shower main body 14 is provided with a water output chamber in communication with a water input pipeline 21 of the shower main body 14; while in a central portion of the water output chamber is provided with a hole to receive the protrusion.

In the present embodiment, the water output chamber includes a water output chamber upper cover 18 and a water output chamber lower cover 19 fastened to each other, the water output chamber upper cover 18 is provided with a water input port 20 in communication with the water input pipeline 21; a tight seal ring 17 is provided at the connection of the water input port 20 and the water input pipeline 21; the water output chamber upper cover 18 is fixed to the shower main body 14 through threading; and a plurality of water output ports are provided on the water output chamber lower cover 19.

In the present embodiment, above the water output chamber upper cover 18 is provided with a fixing claw 16 used for fixing the decoration box.

In the present embodiment, an input port for the water input pipeline 21 of the shower main body 14 is provided with a threaded connector 15.

The present invention also provides a method of implementing a water output device having ultrasonic pulverizing function, comprising the following steps: press down the plastic push button 2, to activate the ultrasonic wave generator 10 to work, such that water and essence in the water box 8 is agitated and vibrated by ultrasonic waves generated, to pass through the web-shape structure in the ultrasonic wave generator 10 allowing only small particles of mist to pass through, to form small particles of water or essence, to provide therapy to a user; when power in the decoration box is used up, perform charging to a charging module 5 through a USB insertion port; and when water is uses up, add water to a water box 8.

The above detailed description of the preferred embodiment is intended to describe more clearly the characteristics and spirit of the present invention. However, the preferred embodiments disclosed above are not intended to be any restrictions to the scope of the present invention. Conversely, its purpose is to include the various changes and equivalent arrangements which are within the scope of the appended claims.

What is claimed is:

1. A water output device having ultrasonic pulverizing function, comprising:
a shower main body, including:
a box, detachably embedded in the shower main body, or forming with the shower main body into a body; and
an ultrasonic pulverizing device, disposed in the box, wherein the ultrasonic pulverizing device includes:
a water box, with its upper portion provided with a water input port, and with its lower portion provided with a water output port;

an ultrasonic wave generator, fixed to a water output port at a lower portion of the water box through a fixing block, for allowing small particles of water mist to pass through; and a control device, disposed at a side of the water box, and including a power source module, a charging module, a vibration circuit module, wherein the charging module and the vibration circuit module are connected respectively to the power source module electrically, the ultrasonic wave generator is connected electrically to the vibration circuit module, while the power source module is fixed in the box using a battery fixing bar.

2. The water output device having ultrasonic pulverizing function as claimed in claim 1, wherein on the vibration circuit module is provided with a press button and an LED lamp; the box includes an upper cover and a lower cover fastening to each other; on the upper cover is provided with a plastic push button, and a lamp hood slot acting in cooperation with the LED lamp.

3. The water output device having ultrasonic pulverizing function as claimed in claim 2, wherein on the side of the box is provided with an input port in communication with the water input port, on the input port is provided with input port tight seal plastic, on a side of the box is further provided with an USB insertion port connected electrically to the charging module, and on the USB insertion port is provided with USB tight seal plastic.

4. The water output device having ultrasonic pulverizing function as claimed in claim 2, wherein a lower portion of the lower cover is protruded downward to form a protrusion, on the protrusion is provided with an output port in communication with the water output port.

5. The water output device having ultrasonic pulverizing function as claimed in claim 4, wherein in a lower portion of the shower main body is provided with a water output chamber in communication with a water input pipeline of the shower main body; while in a central portion of the water output chamber is provided with a hole to receive the protrusion.

6. The water output device having ultrasonic pulverizing function as claimed in claim 5, wherein the water output chamber includes a water output chamber upper cover and a water output chamber lower cover fastened to each other, the water output chamber upper cover is provided with a water input port in communication with the water input pipeline; a tight seal ring is provided at a connection of the water input port and the water input pipeline; the water output chamber upper cover is fixed to the shower main body through threading; and a plurality of water output ports are provided on the water output chamber lower cover.

7. The water output device having ultrasonic pulverizing function as claimed in claim 6, wherein above the water output chamber upper cover is provided with a fixing claw used for fixing the box.

8. The water output device having ultrasonic pulverizing function as claimed in claim 1, wherein an input port for a water input pipeline of the shower main body is provided with a threaded connector.

9. A method of implementing a water output device having ultrasonic pulverizing function as claimed in claim 1, comprising the following steps:

pressing down the plastic push button, to activate the ultrasonic wave generator to work, such that water and essence in the water box is agitated and vibrated by ultrasonic waves generated, to pass through the ultrasonic wave generator allowing only small particles of mist to pass through, to form small particles of the water or essence, hereby providing therapy for a user;

when power in the box is used up, perform charging to the charging module through a USB insertion port; and when water is used up, add water to the water box.

\* \* \* \* \*